US006712617B2

(12) United States Patent
Detmar et al.

(10) Patent No.: US 6,712,617 B2
(45) Date of Patent: Mar. 30, 2004

(54) METHODS OF PREVENTING UVB-INDUCED SKIN DAMAGE

(75) Inventors: Michael J. Detmar, Arlington, MA (US); Kiichiro Yano, Yokohama (JP)

(73) Assignee: The General Hospital Corporation, Boston, MA (US)

( * ) Notice: Subject to any disclaimer, the term of this patent is extended or adjusted under 35 U.S.C. 154(b) by 56 days.

(21) Appl. No.: 10/122,263

(22) Filed: Apr. 11, 2002

(65) Prior Publication Data

US 2003/0008821 A1 Jan. 9, 2003

Related U.S. Application Data

(60) Provisional application No. 60/283,874, filed on Apr. 13, 2001.

(51) Int. Cl.⁷ ............................................. A61K 7/00
(52) U.S. Cl. ...................... 434/407; 424/400; 514/937
(58) Field of Search ................ 424/400, 401; 514/934

(56) References Cited

U.S. PATENT DOCUMENTS 6,025,334 A    2/2000   Dupont 6,372,234 B1    4/2002   Deckers et al.

FOREIGN PATENT DOCUMENTS

WO    WO 00/57899    10/2000

OTHER PUBLICATIONS

Bielenberg et al., "Molecular Regulation of UVB–Induced Cutanoeus Angiogenesis", 1998, The Soc. For Investigative Derm. 111(5) ;874–872.

Brauchle et al., "Ultraviolet B and $H_2$ and $O_2$ Are Potent . . . ", 1996, J. Bio. Chem. 271(36); 21793–21797.

Varani et al., "All–Trans Retinoic Acid Stimulates . . . " 1989, The Soc. For Inestigative Derm.93(4);449–454.

J.J. Voorhees, "Clinical Effects of Long–term Theraphy with . . . ", 1990, International Med. Research 18(suppl. 3);26C–28C.

*Primary Examiner*—Shelley A. Bodson
(74) *Attorney, Agent, or Firm*—Fish & Richardson PC

(57) ABSTRACT

The invention features a method preventing or treating long-term UVB-induced wrinkles in a subject. The method includes inhibiting angiogenesis in the skin of the subject.

17 Claims, No Drawings

METHODS OF PREVENTING UVB-INDUCED SKIN DAMAGE

RELATED APPLICATIONS

This application claims the benefit of U.S. Provisional application serial No. 60/283,874, filed Apr. 13, 2001, the contents of which are incorporated herein by reference in their entirety.

BACKGROUND OF THE INVENTION

Photoaging due to chronic exposure to ultraviolet-B (UVB) irradiation results, inter alia, in the formation of wrinkles.

SUMMARY OF THE INVENTION

The invention is based, in part, on the discovery that inhibition of skin angiogenesis can prevent UVB-induced skin damage, e.g., long term (chronic) UVB induced photoaging, e.g., wrinkle formation, in vivo, in mammals, e.g., humans.

Accordingly, the invention features a method preventing or treating long-term UVB-induced skin damage, e.g., wrinkles, in a subject. The method includes inhibiting angiogenesis in the skin of the subject. In a preferred embodiment, angiogenesis is inhibited before or at the time of a UVB exposure.

In a preferred embodiment, the method also includes identifying a subject, e.g., a mammal, e.g., a human or a non-human mammal, at risk of long term UVB-induced skin damage. The identification of a subject at risk for long term UVB-induced skin damage, e.g., wrinkles, can be performed e.g., by the subject, by a health care provider, or by a provider of cosmetics. The inhibition of angiogenesis can be performed, e.g., by the subject, by a health care provider, or by a provider of cosmetics.

In a preferred embodiment the subject is at least 5 years of age. Preferably, the subject is at least 10, 15, 20, 25, 30, 35, 40, 45, 50, or more years of age.

In a preferred embodiment, wrinkle formation is prevented or reduced.

In a preferred embodiment, angiogenesis is inhibited by increasing the activity of one or more anti-angiogenic factors, e.g., increasing the activity of naturally occurring anti-angiogenic proteins such as TSP-2 or TSP-1 in the subject, thereby preventing wrinkle formation. TSP-2 activity can be increased, e.g., by administering an agent which increases a TSP-2 activity. In a preferred embodiment, an agent which increases a TSP-2 activity can be one or more of the following: a TSP-2 polypeptide, or a biologically active fragment or analog thereof, e.g., a TSP-2 derived polypeptide or retro-inverso polypeptide thereof; a nucleic acid encoding a TSP-2 polypeptide, or a biologically active fragment or analog thereof; an agonist of TSP-2, e.g., an antibody or a small molecule having or increasing TSP-2 activity; or an agent that increases TSP-2 nucleic acid expression, e.g., a small molecule which binds to the promoter region of TSP-2 and increases expression.

In a preferred embodiment, TSP-2 is increased by an agent, e.g., a small molecule, which induces TSP-2 expression. Examples of agents that can induce expression of TSP-2 include fetal calf serum and TGF-α. In preferred embodiments, an agent that induces TSP-2 expression is administered topically. In preferred embodiments, the agent is administered to a subject sufficiently before UVB exposure, e.g., sun exposure, such that an anti-angiogenesis effect is present in the subject's skin at the time of UVB exposure.

TSP-2 activity can also be increased by controlled delivery to the subject of a TSP-2 nucleic acid, or a TSP-2 protein, fragment, or analog. A TSP-2 nucleic acid, protein, fragment, or analog can be administered to the subject in combination with a controlled release device, e.g., a biocompatible polymer, micro particle, or mesh. The device can reduce degradation and control the release of the TSP-2 nucleic acid, protein, fragment, or analog. Such a TSP-2 biocompatible controlled release system can be administered to the subject, e.g., by injection or implantation, e.g., intramuscularly, subcutaneously, intravenously, or at an organ, joint cavity, or at a lesion.

The level of TSP-2 can also be increased by increasing the endogenous TSP-2 activity. Activity can be increased by increasing the level of expression of the gene, e.g., by increasing transcription of the TSP-2 gene; increasing the stability of the TSP-2 mRNA, e.g., by altering the secondary or tertiary structure of the mRNA; increasing the translation of TSP-2 mRNA, e.g., by altering the sequence of the TSP-2 mRNA; and/or increasing the stability of the TSP-2 protein. Transcription of the TSP-2 gene can be increased, e.g., by altering the regulatory sequences of the endogenous TSP-2 gene. In one embodiment the regulatory sequence can be altered by: the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the TSP-2 gene to be transcribed more efficiently.

In a preferred embodiment, the agent is a compound, e.g., small molecule, which induces TSP-2.

TSP-1 activity can be increased, e.g., by administering an agent which increases a TSP-1 activity. In a preferred embodiment, an agent which increases a TSP-1 activity can be one or more of the following: a TSP-1 polypeptide, or a biologically active fragment or analog thereof, e.g., a TSP-1 derived polypeptide or retro-inverso polypeptide thereof; a nucleic acid encoding a TSP-1 polypeptide, or a biologically active fragment or analog thereof; an agonist of TSP-1, e.g., an antibody or a small molecule having or increasing TSP-1 activity; or an agent that increases TSP-1 nucleic acid expression, e.g., a small molecule which binds to the promoter region of TSP-1 and increases expression.

In a preferred embodiment, TSP-1 is increased by an agent, e.g., a small molecule, which induces TSP-1 expression. Examples of agents that can induce expression of TSP-1 include fetal calf serum and TGF-α. In preferred embodiments, an agent that induces TSP-1 expression is administered topically. In preferred embodiments, the agent is administered to a subject sufficiently before UVB exposure, e.g., sun exposure, such that an anti-angiogenesis effect is present in the subject's skin at the time of UVB exposure.

TSP-1 activity can also be increased by controlled delivery to the subject of a TSP-1 nucleic acid, or a TSP-1 protein, fragment, or analog. A TSP-1 nucleic acid, protein, fragment, or analog can be administered to the subject in combination with a controlled release device, e.g., a biocompatible polymer, micro particle, or mesh. The device can reduce degradation and control the release of the TSP-1 nucleic acid, protein, fragment, or analog. Such a TSP-1 biocompatible controlled release system can be administered to the subject, e.g., by injection or implantation, e.g., intramuscularly, subcutaneously, intravenously, or at an organ, joint cavity, or at a lesion.

The level of TSP-1 can also be increased by increasing the endogenous TSP-1 activity. Activity can be increased by increasing the level of expression of the gene, e.g., by increasing transcription of the TSP-1 gene; increasing the stability of the TSP-1 mRNA, e.g., by altering the secondary or tertiary structure of the mRNA; increasing the translation of TSP-1 mRNA, e.g., by altering the sequence of the TSP-1 mRNA; and/or increasing the stability of the TSP-1 protein. Transcription of the TSP-1 gene can be increased, e.g., by altering the regulatory sequences of the endogenous TSP-1 gene. In one embodiment the regulatory sequence can be altered by: the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the TSP-1 gene to be transcribed more efficiently.

In a preferred embodiment, the agent is a compound, e.g., small molecule, which induces TSP-1.

In a preferred embodiment, the agent which increases the activity of one or more anti-angiogenic factors, e.g., by inducing the activity of a naturally occurring anti-angiogenic protein such as TSP-2 or TSP-1 is administered, e.g., by topically administering the agent; systemically administering the agent; orally administering the agent; or injecting the agent, preferably dermally or subcutaneously. In preferred embodiments, the agent is administered using a suitable delivery vehicle. Preferably, the agent is included in a composition for topical use, e.g., the composition is a gel, cream, or liquid. The composition can further include a cosmetic ingredient, e.g., a fragrance or a sunscreen, e.g., octyl methoxycinnamate, aminobenzoic acid, oxybenzone, padimate O, homosalate, or titanium dioxide. The composition can also include a plant extract, e.g., aloe extract, grape extract. The composition can also include a vitamin, e.g., a vitamin A, e.g., retinol; a vitamin C, e.g., L-ascorbic acid or L-ascorbic acid palmitate; a vitamin E, e.g., tocopherol acetate.

In a preferred embodiment, the agent is administered to the subject sufficiently before UVB exposure, e.g., sun exposure, such that an anti-angiogenesis effect is present at the time of UVB exposure.

In another preferred embodiment, administration of the agent that increases the activity of one or more anti-angiogenic factors, e.g., by inducing the activity of a naturally occurring anti-angiogenic protein such as TSP-2 or TSP-1, is repeated, e.g., is repeated at least 1, 2, 3, 5, 10, 20 or more times over at least as many days. In a preferred embodiment, the agent is administered chronically. In a preferred embodiment, the agent is administered at least once a week, preferably 2, 3, 4, 5 times a week or daily for at least two weeks, preferably for at least 1, 2, 3, 4, 5, or 6 months. For example, the agent is administered periodically over 3–12 weeks, e.g., it is administered throughout the summer. In a preferred embodiment, the agent is administered to and wrinkles are inhibited or prevented on one or more of: the subject's face, neck, chest, ears, hands, bald spots of the scalp, or any other skin that is exposed to UVB radiation.

In a preferred embodiment, the subject has been, or will be, exposed to long term UVB radiation.

In a preferred embodiment, the subject shows one or more signs of photoaging, e.g., wrinkles, lines, sagging, freckles, tanned skin, discoloration, hyperpigmentation, age spots, e.g., "liver spots", thinning of the skin, cataracts, epidermal hyperplasia, skin elastosis, degradation of extracellular matrix, or precancerous or cancerous skin growths (actinic keratoses, solar keratoses).

In a preferred embodiment, angiogenesis is inhibited by decreasing VEGF activity in the subject, e.g., by inhibiting signaling through the VEGF receptor, e.g., through KDR; by inhibiting the level of VEGF protein; decreasing the levels of VEGF gene expression; and/or decreasing VEGF protein production and/or activity, in the subject, thereby preventing UVB-induced skin damage, e.g., long term-UVB induced skin damage, e.g., wrinkle formation.

In a preferred embodiment, VEGF is inhibited by administering an agent which inhibits VEGF activity. An agent which inhibits VEGF activity can be one or more of: an agent, e.g., a small molecule, that inhibits a VEGF receptor, e.g., by inhibiting binding of VEGF to its receptor or by inhibiting VEGF receptor signaling; a VEGF nucleic acid molecule which can bind to a cellular VEGF nucleic acid sequence, e.g., mRNA, and inhibit expression of the protein, e.g., an antisense molecule or VEGF ribozyme; an antibody that specifically binds to VEGF protein, e.g., an antibody that disrupts VEGF's ability to bind to its natural cellular target; an agent which decreases VEGF gene expression, e.g., a small molecule which binds the promoter of VEGF.

In another preferred embodiment, VEGF activity is inhibited by decreasing the level of expression of an endogenous VEGF gene, e.g., by decreasing transcription of the VEGF gene. In a preferred embodiment, transcription of the VEGF gene can be decreased by: altering the regulatory sequences of the endogenous VEGF gene, e.g., by the addition of a negative regulatory sequence (such as a DNA-binding site for a transcriptional repressor).

In another preferred embodiment, the agent is a compound, e.g., a small molecule, which inhibits VEGF activity, e.g., by inhibiting VEGF receptor signaling, or by interacting, directly or indirectly, with a VEGF promoter.

In a preferred embodiment, the agent which inhibits VEGF expression is administered, e.g., by topically administering the agent; systemically administering the agent; orally administering the agent; or injecting the agent, preferably dermally or subcutaneously. In preferred embodiments, the agent is administered using a suitable delivery vehicle. Preferably, the agent is included in a composition for topical use, e.g., the composition is a gel, cream, or liquid. The composition can further include a cosmetic ingredient, e.g., a fragrance or a sunscreen, e.g., octyl methoxycinnamate, aminobenzoic acid, oxybenzone, padimate O, homosalate, or titanium dioxide. The composition can also include a plant extract, e.g., aloe extract, grape extract. The composition can also include a vitamin, e.g., a vitamin A, e.g., retinol; a vitamin C, e.g., L-ascorbic acid or L-ascorbic acid palmitate; a vitamin E, e.g., tocopherol acetate. In a preferred embodiment, an agent that inhibits VEGF expression is administered topically. In a preferred embodiment, the agent is applied sufficiently before UVB, e.g., sun, exposure such that an anti-angiogenesis effect is present at the time of UVB exposure.

In another preferred embodiment, administration of the agent is repeated, e.g., is repeated at least 1, 2, 3, 5, 10, 20 or more times. In a preferred embodiment, the agent is applied chronically. In a preferred embodiment, the agent is applied at least once a week, preferably 2, 3, 4, 5 times a week or daily for at least two weeks, preferably for at least 1, 2, 3, 4, 5, or 6 months. For example, the agent is administered periodically over 3–12 weeks, e.g., it is administered throughout the summer. In a preferred embodiment, wrinkles are inhibited on: the subject's face, neck, chest, hands, or any other skin that has been exposed to UVB radiation.

In a preferred embodiment the method includes administering one or a more of an agent which increases TSP-2 activity, an agent which increases TSP-1 activity, or an agent which inhibits VEGF. In preferred embodiments, one or more inhibitors of angiogenesis, e.g., one or more agents that induce or increase an anti-angiogenesis inhibitor, are administered.

In another aspect, the invention features a method of preventing or treating UVB-induced skin damage, e.g., long term UVB-induced skin damage, e.g., wrinkles, in a subject. The method includes administering to the subject, e.g., topically, a composition comprising an inhibitor of angiogenesis, e.g., an agent, e.g., a small molecule, that increases or induces an inhibitor of angiogenesis, or an agent, e.g., a small molecule, that inhibits an angiogenic molecule, in an amount sufficient to reduce or prevent UVB-induced skin damage, e.g., long term UVB-induced skin damage, e.g, wrinkles. In a preferred embodiment, the agent is administered sufficiently before UVB exposure, e.g., sun exposure, such that an anti-angiogenesis effect is present at the time of UVB exposure.

In a preferred embodiment, the agent is a compound, e.g., small molecule, which induces TSP-2.

In a preferred embodiment, the agent is a compound, e.g., a small molecule, that inhibits VEGF.

In a preferred embodiment, the agent is administered topically. The agent can be administered to the face, chest, ears, neck, hands, bald areas of the scalp, and other regions of the body. The treatment can involve more than one administration, e.g., at least two, three, or four administrations, of the angiogenesis inhibitor. The treatment can also involve daily administration of the angiogenesis inhibitor.

In a preferred embodiment, the inhibitor of angiogenesis, e.g. the agent that increases or induces the inhibitor of angiogenesis, is provided in a sterile composition.

In a preferred embodiment, the inhibitor of angiogenesis is TSP-2.

In a preferred embodiment, the inhibitor of angiogenesis is TSP-1.

In a preferred embodiment, the composition further includes a cosmetic ingredient, e.g., a fragrance, or a sunscreen, e.g., octyl methoxycinnamate, aminobenzoic acid, oxybenzone, padimate O, homosalate, or titanium dioxide. The composition can also include a plant extract, e.g., aloe extract, grape extract. The composition can also include a vitamin, e.g., a vitamin A, e.g., retinol; a vitamin C, e.g., L-ascorbic acid or L-ascorbic acid palmitate; a vitamin E, e.g., tocopherol acetate.

In a preferred embodiment, the composition is administered chronically. In a preferred embodiment, the composition is applied at least once a week, preferably 2, 3, 4, 5 times a week or daily for at least two weeks, preferably for at least 1, 2, 3, 4, 5, or 6 months. For example, the composition is applied throughout periodically over 3–12 weeks, e.g., throughout the summer. In a preferred embodiment the method includes administering one or a more of an agent which increases TSP-2 activity, an agent which increases TSP-1 activity, or an agent which inhibits VEGF. In preferred embodiments one or more inhibitors of angiogenesis are administered.

In another aspect, the invention features a method of preventing UVB-induced skin damage, e.g., long term-UVB induced skin damage, e.g., a wrinkle, in a subject. The method includes identifying a subject in need of protection from UVB-induced skin damage, e.g., long term-UVB induced skin damage, e.g., protection from wrinkle formation; administering an inhibitor of angiogenesis, e.g., an agent, e.g., a small molecule, that increases or induces an inhibitor of angiogenesis or an agent, e.g., a small molecule, that inhibits an angiogenic molecule, to the subject; and evaluating the effect of the administration on wrinkle formation. The identification of a subject in need of protection from long term UVB-induced skin damage, e.g., wrinkles, can be performed e.g., by the subject, by a health care provider, or by a provider of cosmetics. The administration of an inhibitor of angiogenesis and the evaluation of the effect of the administration on wrinkle inhibition can be performed, e.g., by the subject, by a health care provider, or by a provider of cosmetics.

In a preferred embodiment, the inhibitor of angiogenesis is TSP-2.

In a preferred embodiment, the inhibitor of angiogenesis is TSP-1.

In a preferred embodiment, the angiogenic molecule is VEGF.

In a preferred embodiment, the wrinkle is caused by exposure to UVB radiation.

In a preferred embodiment, the agent is administered topically. In a preferred embodiment, the agent is administered sufficiently before UVB exposure, e.g., sun exposure, such that an anti-angiogenesis effect is present at the time of UVB exposure.

In a preferred embodiment, the agent is applied chronically. In a preferred embodiment, the agent is applied at least once a week, preferably 2, 3, 4, 5 times a week or daily for at least two weeks, preferably for at least 1, 2, 3, 4, 5, or 6 months. For example, the agent is applied periodically over 3–12 weeks, e.g., throughout the summer.

In a preferred embodiment, the inhibitor of angiogenesis, e.g., agent that induces an inhibitor of angiogenesis, is provided in a sterile composition.

In a preferred embodiment the method includes administering one or a more of an agent which increases TSP-2 activity, an agent which increases TSP-1 activity (TSP-1 activity can be increased by methods analogous to those described herein for increasing TSP-2 activity), or an agent which inhibits VEGF. In preferred embodiments one or more inhibitors of angiogenesis are administered.

In another aspect, the invention features a method of evaluating a test compound for the ability to induce the expression of an anti-angiogenic protein, e.g., TSP-1 or TSP-2, e.g., induce it in the skin. The method includes: providing a cell, e.g., an epidermal cell, having a transgene which includes a nucleic acid which encodes a reporter molecule functionally linked to a control region, e.g., a promoter, of an anti-angiogenesis gene, e.g., TSP-1 or TSP-2, where the reporter molecule is other than the protein encoded by the gene normally associated with the promoter; contacting the cell with a test compound; and evaluating a signal produced by the reporter molecule, the presence or strength of which is correlated with modulation of expression of the anti-angiogenesis gene by the test compound. The compound can be a protein, a polypeptide, a small molecule, e.g., a small molecule of molecular weight less than 2000 daltons, preferably less than 1000 daltons.

In a preferred embodiment, the reporter is a molecule that can provide a fluorescent signal. The reporter can be, e.g., luciferase, GFP, or BFP. In other embodiments, the reporter is an enzyme.

In a preferred embodiment, the cell is a cultured cell, e.g., an immortalized human epidermal keratinocyte.

In a preferred embodiment, the cell is from a transgenic animal.

In a preferred embodiment, the cell is from a transgenic animal and the test compound is administered to the transgenic animal, e.g., is applied topically to the skin of the transgenic animal.

In a preferred embodiment, the method further includes testing the compound in vivo on a human or non-human animal, e.g., by administering the compound to the animal, exposing the animal to UVB, and evaluating the effect of the compound.

In another aspect, the invention features a method of evaluating a test compound for the ability to inhibit the expression of an angiogenic protein, e.g., VEGF, e.g., inhibit it in the skin. The method includes: providing a cell, e.g., an epidermal cell, having a transgene which includes a nucleic acid which encodes a reporter molecule functionally linked to a control region, e.g., a promoter, of an angiogenic factor gene, e.g., VEGF, where the reporter molecule is other than the protein encoded by the gene normally associated with the promoter; contacting the cell with a test compound; and evaluating a signal produced by the reporter molecule, the presence or strength of which is correlated with modulation of expression of the angiogenesis gene by the test compound. The compound can be a protein, a polypeptide, a small molecule, e.g., a small molecule of molecular weight less than 2000 daltons, preferably less than 1000 daltons, more preferably less than 500 daltons.

In a preferred embodiment, the reporter is a molecule that can provide a fluorescent signal. The reporter can be, e.g., luciferase, GFP, or BFP. In other embodiments, the reporter is an enzyme.

In a preferred embodiment, the cell is a cultured cell, e.g., an immortalized human epidermal keratinocyte.

In a preferred embodiment, the cell is from a transgenic animal.

In a preferred embodiment, the cell is from a transgenic animal and the test compound is administered to the transgenic animal, e.g., is applied topically to the skin of the transgenic animal.

In a preferred embodiment, the method further includes testing the compound in vivo on a human or non-human animal, e.g., by administering the compound to the animal, exposing the animal to UVB, and evaluating the effect of the compound.

In another aspect, the invention features a composition for preventing or treating UVB-induced skin damage, e.g., wrinkles. The composition includes an inhibitor of angiogenesis (e.g., TSP-1 or TSP-2), e.g., an agent, e.g., a small molecule, that increases or induces TSP-1 or TSP-2; or an agent, e.g., a small molecule, that inhibits an angiogenic molecule, e.g., an agent that inhibits VEGF, and a pharmaceutically acceptable carrier. Preferably, the composition is sterile.

In a preferred embodiment, the agent is a compound, e.g., small molecule, which induces TSP-2.

In a preferred embodiment, the composition is administered topically.

In a preferred embodiment, the inhibitor of angiogenesis is TSP-2.

In a preferred embodiment, the inhibitor of angiogenesis is TSP-1.

In a preferred embodiment one or a more of: an agent which increases TSP-2 activity, an agent which increases TSP-1 activity, or an agent which inhibits VEGF activity are included. In preferred embodiments one or more inhibitors of angiogenesis are included.

In a preferred embodiment, the composition also includes a cosmetic ingredient, e.g., a fragrance, a humectant, or a sunscreen, e.g., octyl methoxycinnamate, aminobenzoic acid, oxybenzone, padimate O, homosalate, or titanium dioxide. The composition can also include a plant extract, e.g., aloe extract, grape extract. The composition can also include a vitamin, e.g., a vitamin A, e.g., retinol; a vitamin C, e.g., L-ascorbic acid or L-ascorbic acid palmitate; a vitamin E, e.g., tocopherol acetate.

In another aspect, the invention features a method of providing protection from UVB-induced skin damage, e.g., long term UVB-induced skin damage, e.g., wrinkle protection, to a subject. The method includes supplying to the subject a composition that includes an inhibitor of angiogenesis, e.g., an agent, e.g., a small molecule, that increases or induces an inhibitor of angiogenesis, e.g., TSP-2 or TSP-1 or an agent, e.g., a small molecule, that inhibits an angiogenic molecule, e.g., an agent that inhibits VEGF; and supplying to the subject instructions for using the composition to prevent or reduce UVB-induced skin damage, e.g., long term UVB-induced skin damage, e.g., wrinkles.

In a preferred embodiment, the instructions include directions to apply the composition to the skin prior to and/or during sun exposure.

In a preferred embodiment, the instructions include directions to apply the composition chronically. In a preferred embodiment, the instructions include directions to apply the composition at least once a week, preferably 2, 3, 4, 5 times a week or daily for at least two weeks, preferably for at least 1, 2, 3, 4, 5, or 6 months. For example, the instructions can include instructions to apply the composition periodically over 3–12 weeks, e.g., throughout the summer.

In a preferred embodiment, the inhibitor of angiogenesis is TSP-2.

In a preferred embodiment, the inhibitor of angiogenesis is TSP-1.

In a preferred embodiment, the agent is a compound, e.g., small molecule, which induces TSP-2 or TSP-1.

In a preferred embodiment, the composition further comprises a cosmetic ingredient, e.g., a fragrance, or a sunscreen, e.g., octyl methoxycinnamate, aminobenzoic acid, oxybenzone, padimate O, homosalate, or titanium dioxide. The composition can also include a plant extract, e.g., aloe extract, grape extract. The composition can also include a vitamin, e.g., a vitamin A, e.g., retinol; a vitamin C, e.g., L-ascorbic acid or L-ascorbic acid palmitate; a vitamin E, e.g., tocopherol acetate.

In a preferred embodiment, the composition includes one or a more of an agent which increases TSP-2 activity, an agent which increases TSP-1 activity, or an agent which inhibits VEGF. In preferred embodiments the composition includes one or more inhibitors of angiogenesis.

In another aspect, the invention features a kit for preventing UVB-induced skin damage, e.g., long term UVB-induced skin damage, e.g., wrinkles in a subject. The kit includes a composition including an inhibitor of angiogenesis, e.g., an agent, e.g., a small molecule, that increases or induces an inhibitor of angiogenesis; and instructions for using the composition to prevent UVB-induced skin damage, e.g., long term UVB-induced skin damage, e.g., wrinkles.

In a preferred embodiment, the agent is a compound, e.g., small molecule, which induces TSP-2.

In a preferred embodiment, the instructions include directions to apply the composition to the skin prior to and/or during sun exposure.

In a preferred embodiment, the instructions include directions to apply the composition chronically. In a preferred embodiment, the instructions include directions to apply the composition at least once a week, preferably 2, 3, 4, 5 times a week or daily for at least two weeks, preferably for at least 1, 2, 3, 4, 5, or 6 months. For example, the instructions can include instructions to apply the composition periodically over 3–12 weeks, e.g., throughout the summer.

In a preferred embodiment, the inhibitor of angiogenesis is TSP-2.

In a preferred embodiment, the inhibitor of angiogenesis is TSP-1.

In a preferred embodiment, the composition also includes a cosmetic ingredient, e.g., a fragrance, a moisturizer, or a sunscreen, e.g., octyl methoxycinnamate, aminobenzoic acid, oxybenzone, padimate O, homosalate, or titanium dioxide. The composition can also include a plant extract, e.g., aloe extract, grape extract. The composition can also include a vitamin, e.g., a vitamin A, e.g., retinol; a vitamin C, e.g., L-ascorbic acid or L-ascorbic acid palmitate; a vitamin E, e.g., tocopherol acetate.

In a preferred embodiment, the instructions include directions to apply the composition to the skin, e.g., exposed skin, e.g., the face, neck, hands, ears, chest, or bald areas of the scalp. Preferably, the instructions include directions to apply the composition before and/or during UVB, e.g., sun, exposure.

In a preferred embodiment, the composition includes one or a more of an agent which increases TSP-2 activity, an agent which increases TSP-1 activity, or an agent which inhibits VEGF. In preferred embodiments the composition includes one or more inhibitors of angiogenesis.

A wrinkle, as used herein, is a configuration change in the surface of the skin. There may or may not be a specific structural alterations at the histological level of a wrinkle. Wrinkles can be classified as described in Kligman et al. (1985) *Br J Derm* 113:37–42, herein incorporated by reference. Kligman classifies wrinkles into three classes: linear wrinkles, glyphic wrinkles, and crinkles. Linear wrinkles are straight, found generally in the facial skin, and are caused by natural aging and exposure to ultraviolet light. Glyphic wrinkles are shaped as apparent triangles or rectangles of wrinkles, are found on the face, hands, and neck exposed to sunlight, and are aggravated by exposure to ultraviolet light or dermatoheliosis. Crinkles are thin, crinkled wrinkles on flabby skin, found anywhere on the skin, but typically on the backs of hands and around the eyelids. Wrinkles include, and are sometimes referred to as, lines, fine wrinkles, crinkles, crow's feet, or sags.

The term "small molecule", as used herein, includes peptides, peptidomimetics, or non-peptidic compounds, such as organic molecules, having a molecular weight less than 2,000, preferably less than 1,000 daltons.

Treating, as used herein, can mean total or partial alleviation or elimination of a symptom or effect of a disorder. Preventing, as used herein, can mean complete prevention, or a delay in the appearance, of a symptom or effect of a disorder.

As used herein, exposure to long-term (or chronic) UVB-radiation means chronic exposure to natural sunlight or artificial UVB radiation (e.g., a UVB sun lamp, e.g., for tanning, or for phototherapy, e.g., for treatment of psoriasis, atopic dermatitis, or vitiligo). For example, chronic exposure can be exposure to the sun at a UV index of 3–6, or higher, for at least 10 minutes at least 3, more preferably at least 5, or at least 10 times in a preselected period of time. The preselected period of time can be 1 month, 2 months, 3 months, 6 months, 12 months or 24 months, e.g., exposure to a cumulative 5 hours of UVB radiation, e.g., sunlight or artificial UVB radiation, in a 12 month period. A subject at risk of long term UV-induced damage, e.g., wrinkles, can be a subject who has been, or will be, exposed to at least 10 minutes of sun at a UV index of 3–6, or higher, at least 10 times during a one year period, or a subject who has been or will be exposed to a cumulative 5 hours of UVB radiation in one year. Preferably, the subject is exposed to at least 30 minutes of UVB radiation at least 20 times a year for at least 3 years. Preferably, the subject is exposed to the sun between 11 A.M. and 3 P.M., or the subject is exposed to the sun during the summer months, or the subject is exposed to the sun on days of high to extreme UV index. A subject at risk for long term UVB induced skin damage, e.g., wrinkles, includes, e.g., a person who lives at a high altitude, e.g., a person who lives at least 1000 feet above sea level; a person who lives near the equator, e.g., within 1000 miles from the equator; a person who participates in outdoor sports at least 10 times in one year, e.g., a person who participates in jogging, playing tennis, mountain climbing; snow skiing, or water skiing; a person who is undergoing or has undergone UVB phototherapy.

DETAILED DESCRIPTION

Exposure to UVB Radiation

The major source of UVB radiation is natural sunlight. The intensity of UVB rays varies depending on the time of day, time of year, the sun's position in the sky, altitude and distance from the equator. These rays are most intense during the midday hours in the summer, although they are always present, even during the winter months. Distance above sea level and distance from the equator are also important to consider. The higher the altitude the greater the intensity of UVB rays. Therefore, mountaineers, skiers, and those who live at high altitudes are at risk of long term UVB damage. Also, the nearer one is to the equator the more intense the UV radiation and the higher the risk of long term UVB damage.

Snow, water, and sand reflect sunlight, magnifying the amount of UVB radiation that reaches the skin. Even when clouds obscure the sun, UVB levels can still be sufficiently high to cause photoaging, e.g., wrinkles, upon long term exposure.

The UV index (developed by the Environmental Protection Agency) indicates the intensity of the sun's UV rays on a given day. There are four categories—moderate (UV index is less than 3), high (UV index is 3 to 6) very high (UV index is 6 to 10) and extreme (UV index is greater than 10). A moderate UV Index means it will take more than an hour to burn your skin; an extreme level means it will take less than 15 minutes. The index is often included with weather reports. Clinically, UVB exposure is measured in MEDs. One MED is the amount of UVB required to produce a sunburn in sensitive skin. Because the effects of UVB exposure are cumulative, long term or chronic UVB induced wrinkles can occur as a result of long term exposure to UVB levels below those which, upon acute exposure, can cause erythema or edema or burning (e.g., below one MED). For example, a subject is at risk of long term UVB induced wrinkles if the subject is chronically exposed to the sun even if the subject is only exposed to the sun during days with a low or moderate UV Index.

Angiogenesis and Chronic UVB Exposure

Photoaged skin is characterized by epidermal hyperplasia, dermal elastosis and matrix protein degradation (5, 38), and by the presence of a perivenular lymphohistocytic dermal infiltrates (23). Results described herein reveal that chronic UVB irradiation of the skin is associated with pronounced cutaneous angiogenesis and with increased VEGF expression in the hyperplastic epidermis, and that targeted inhibition of skin angiogenesis by TSP-1 prevents UVB-induced dermal damage and wrinkle formation.

After 10 weeks of UVB irradiation of Skh-1 hairless mice, an established experimental model for chronic photoaging (26), we found pronounced wrinkle formation and the characteristic histological features of epidermal and dermal hyperplasia, associated with increased detection of disorganized elastic and collagen fibers in the dermis. Computer-assisted quantitative image analysis (24) of tissue sections stained for the endothelial junction molecule CD31 (39) revealed a marked induction of skin angiogenesis after long-term UVB irradiation, with a significant increase of both vessel density and vessel size. These vascular changes were comparable to the angiogenic changes which occur during cutaneous wound healing where both sprouting of preexisting blood vessels and vessel enlargement contribute to the formation of the vessel-rich granulation tissue (24). In contrast, chronic inflammatory skin diseases such as psoriasis predominantly show vascular remodeling with elongation and enlargement of cutaneous microvessels but without the formation of new vessel sprouts. These findings indicate that chronic UVB irradiation of the skin results in a chronic tissue repair reaction and they suggest that angiogenesis might play an important role in the mediation of UVB-induced skin damage.

Vascular endothelial growth factor (VEGF) has been identified as a major, keratinocyte-derived skin angiogenesis factor (40) with increased expression in the hyperplastic epidermis of lesional psoriatic skin (12) and of other skin diseases associated with dermal angiogenesis (14, 41), as well as in the neo-epidermis of healing wounds (13, 42). In the experiments described herein, a pronounced upregulation of VEGF mRNA expression was found in the hyperplastic epidermis of chronically UVB-irradiated skin, preferentially in suprabasal keratinocytes. These findings are in accordance with previous reports that acute UVB irradiation induced VEGF expression in human epidermal keratinocyte in vitro (43) (44) and in vivo (7).

Angiogenesis and Chronic UVB-Induced Wrinkles

Transgenic mice with skin-specific overexpression of the angiogenesis inhibitor TSP-1 were exposed to chronic UVB irradiation. Using an established keratin 14 (K14) promoter cassette to target TSP-1 transgene expression to epidermal keratinocytes, we have previously established K14/TSP-1 transgenic mice which are characterized by increased levels of epidermal TSP-1 expression, by normal thickness and morphology of the epidermis and dermis and by potent inhibition of skin angiogenesis during cutaneous wound healing (24). The use of the K14 promoter ensures high transgene expression under conditions of epidermal hyperplasia because K14 gene expression is greatly enhanced in proliferating keratinocytes. Results described in the Examples herein revealed that epidermal overexpression of TSP-1 potently inhibited dermal photodamage and collagen and elastic fiber disorganization, and also completely inhibited the formation of skin wrinkles. This was associated with a potent inhibition of skin angiogenesis and with decreased endothelial proliferation rates and with increased apoptosis of endothelial cells. Together, these results indicate that inhibition of the repair-associated, UVB-induced angiogenesis also prevents dermal photodamage including the formation of wrinkles.

It has been previously shown that TSP-1 mediates inhibition of angiogenesis by specific interactions of distinct sequences within the type I repeats with the CD36 receptor on endothelial cells, resulting in enhanced endothelial cell apoptosis rates (46). Recent evidence suggests that TSP-1, similar to the related molecule TSP-2 (47), can also inhibit the activation of matrix metalloproteinase-2 (MMP-2), with important implications for its antiangiogenic effects (48, 49). These results identify an additional mechanism by which TSP-1, through inhibition of MMP-9 activation, may reduce cutaneous angiogenesis induced by UVB irradiation. MMP-9 is a member of a zinc proteinase family of molecules that digest components of the extracellular matrix, and increased levels of MMP-9 expression and activity have been found in UV irradiated human skin (35, 50, 51).

Conversely, TSP-2 knock out mice showed increased wrinkling in response to long term UVB exposure, as compared to wildtype mice. However, no major differences in MMP-9 activity were detected between TSP-2 knock out mice and wildtype mice after chronic UVB irradiation. These results suggest that the specific inhibition of skin angiogenesis (as opposed to MMP effects) may represent a promising new approach for the prevention of chronic UVB damage, e.g., wrinkles, to the skin.

Analogs of TSP

Analogs can differ from naturally occurring TSP-1 or TSP-2 in amino acid sequence or in ways that do not involve sequence, or both. Non-sequence modifications include in vivo or in vitro chemical derivatization of TSP-1 or TSP-2. Non-sequence modifications include changes in acetylation, methylation, phosphorylation, carboxylation, or glycosylation.

The sequence of TSP-1 and TSP-2, e.g., human TSP-1 and TSP-2, are known in the art. Preferred analogs include TSP-1 or TSP-2 (or biologically active fragments thereof) whose sequences differ from the wild-type sequence by one or more conservative amino acid substitutions or by one or more non-conservative amino acid substitutions, deletions, or insertions which do not abolish the TSP-1 or TSP-2 biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |

TABLE 1-continued

CONSERVATIVE AMINO ACID REPLACEMENTS

| For Amino Acid | Code | Replace with any of |
|---|---|---|
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met,D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

Production of Fragments and Analogs

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc* 3rd *Cleveland Sympos. Macromolecules,* ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* (1978) USA, 75: 5765).

Cassette Mutagenesis

Another method for preparing variants, cassette mutagenesis, is based on the technique described by Wells et al. (*Gene* (1985) 34:315). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, assembly into a trimeric molecules, binding to natural ligands, e.g., a receptor or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays can be used to identify a protein that interacts with VEGF. These may include agonists, superagonists, and antagonists. (The subject protein and a protein it interacts with are used as the bait protein and fish proteins.). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., a TSP-1 or TSP-2 molecule or a fragment thereof. The second hybrid protein contains a transcriptional activation domain fused to a "fish" protein, e.g. an expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080–1083). Surface proteins of other bacterial species have also served as peptide fusion partners. Examples include the Staphylococcus protein A and the outer membrane protease IgA of Neisseria (Hansson et al. (1992) *J. Bacteriol.* 174, 4239–4245 and Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

Secondary Screens

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest, e.g., TSP 1 or TSP2, and a ligand can be used to identify agonists or antagonists from a group of peptide fragments isolated though one of the primary screens described above. For example, the ability of a test compound to inhibit angiogenesis in the skin can be tested by a number of methods known in the art, e.g., by applying a test compound or treatment to the skin of a subject e.g., an experimental animal (e.g., a mouse); and evaluating the number and/or size of blood vessels in the skin of the subject in the absence compared to in the presence of the compound. A compound that causes a decrease in the number or size of blood vessels in the skin of the subject is identified as a compound that inhibits angiogenesis in the skin.

Therefore, methods for generating fragments and analogs and testing them for activity are known in the art. Once the core sequence of interest is identified, it is routine for one skilled in the art to obtain analogs and fragments and to test them for the desired activity.

Peptide Mimetics

The invention also provides for reduction of the protein binding domains of the subject TSP-1 or TSP-2 polypeptides to generate mimetics, e.g. peptide or non-peptide agents. See, for example, "Peptide inhibitors of human papillomavirus protein binding to retinoblastoma gene protein" European patent applications EP 0 412 762 and EP 0 031 080.

Non-hydrolyzable peptide analogs of critical residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Fusion Proteins

Polypeptides for modulating the level of TSP-1 or TSP-2 protein can be fused to another protein or portion thereof. For example, a TSP-1 or TSP-2 protein or portion thereof, can be operably linked to another polypeptide moiety to enhance solubility. Examples of a protein which can be fused with TSP-1 or TSP-2 or portions thereof include a plasma protein or fragment thereof, which can improve the circulating half life of VEGF. For example, the fusion protein can be a TSP-1 or TSP-2-immunoglobulin (Ig) fusion protein in which the TSP-1 or TSP-2 sequence is fused to a sequence derived from the immunoglobulin superfamily. Several soluble fusion protein constructs have been disclosed wherein the extracellular domain of a cell surface glycoprotein is fused with the constant F(c) region of an immunoglobulin. For example, Capon et al. (1989) *Nature* 337(9):525–531, provide guidance on generating a longer lasting CD4 analog by fusing CD4 to an immunoglobulin (IgG1). See also, Capon et al., U.S. Pat. Nos. 5,116,964 and 5,428,130 (CD4-IgG fusion constructs); Linsley et al., U.S. Pat. No. 5,434,131 (CTLA4-IgG1 and B7-IgG1 fusion constructs); Linsley et al. (1991) *J. Exp. Med.* 174:561–569 (CTLA4-IgG1 fusion constructs); and Linsley et al. (1991) *J. Exp. Med* 173:721–730 (CD28-IgG1 and B7-IgG1 fusion constructs). Such fusion proteins have proven useful for modulating receptor-ligand interactions and reducing inflammation in vivo. For example, fusion proteins in which an extracellular domain of cell surface tumor necrosis factor receptor (TNFR) proteins has been fused to an immunoglobulin constant (Fc) region have been used in vivo. See, for example, Moreland et al. (1997) *N. Engl. J. Med.* 337(3):141–147; and, van der Poll et al. (1997) *Blood* 89(10):3727–3734).

Antisense Nucleic Acid Sequences

Nucleic acid molecules which are antisense to a nucleotide encoding a positive angiogenesis factor, e.g., VEGF, can be used as an agent which inhibits angiogenesis in the methods described herein. An "antisense" nucleic acid includes a nucleotide sequence which is complementary to a "sense" nucleic acid encoding a positive angiogenesis factor, e.g., VEGF, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire VEGF coding strand, or to only a portion thereof. For example, an antisense nucleic acid molecule which antisense to the "coding region" of the coding strand of a nucleotide sequence encoding VEGF can be used.

The coding strand sequences encoding VEGF are known. Given the coding strand sequences encoding VEGF, antisense nucleic acids can be designed according to the rules of Watson and Crick base pairing. The antisense nucleic acid molecule can be complementary to the entire coding region of VEGF mRNA, but more preferably is an oligonucleotide which is antisense to only a portion of the coding or noncoding region of VEGF mRNA. For example, the antisense oligonucleotide can be complementary to the region surrounding the translation start site of VEGF mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest.

RNAi

Double stranded nucleic acid molecules that can silence a gene encoding a component of the IR signaling pathway described herein, e.g., a component described herein, can also be used as an agent which inhibits expression of the component of the IR signaling pathway. RNA interference (RNAi) is a mechanism of post-transcriptional gene silencing in which double-stranded RNA (dsRNA) corresponding to a gene (or coding region) of interest is introduced into a cell or an organism, resulting in degradation of the corresponding mRNA. The RNAi effect persists for multiple cell divisions before gene expression is regained. RNAi is therefore an extremely powerful method for making targeted knockouts or "knockdowns" at the RNA level. RNAi has proven successful in human cells, including human embryonic kidney and HeLa cells (see, e.g., Elbashir et al. Nature May 24, 2001;411(6836):494–8). In one embodiment, gene silencing can be induced in mammalian cells by enforcing endogenous expression of RNA hairpins (see Paddison et al., 2002, *PNAS USA* 99:1443–1448). In another embodiment, transfection of small (21–23 nt) dsRNA specifically inhibits gene expression (reviewed in Caplen (2002) Trends in Biotechnology 20:49–51).

Briefly, RNAi is thought to work as follows. dsRNA corresponding to a portion of a gene to be silenced is introduced into a cell. The dsRNA is digested into 21–23 nucleotide siRNAs, or short interfering RNAs. The siRNA duplexes bind to a nuclease complex to form what is known as the RNA-induced silencing complex, or RISC. The RISC targets the homologous transcript by base pairing interactions between one of the siRNA strands and the endogenous mRNA. It then cleaves the mRNA~12 nucleotides from the 3' terminus of the siRNA (reviewed in Sharp et al (2001) *Genes Dev* 15: 485–490; and Hammond et al. (2001) *Nature Rev Gen* 2: 110–119).

RNAi technology in gene silencing utilizes standard molecular biology methods. dsRNA corresponding to the sequence from a target gene to be inactivated can be produced by standard methods, e.g., by simultaneous transcription of both strands of a template DNA (corresponding to the target sequence) with T7 RNA polymerase. Kits for production of dsRNA for use in RNAi are available commercially, e.g., from New England Biolabs, Inc. Methods of transfection of dsRNA or plasmids engineered to make dsRNA are routine in the art.

Gene silencing effects similar to those of RNAi have been reported in mammalian cells with transfection of a mRNA-cDNA hybrid construct (Lin et al., Biochem Biophys Res Commun Mar. 2, 2001;281(3):639–44), providing yet another strategy for gene silencing.

Administration

An agent which modulates angiogenesis, e.g., an angiogenesis inhibitor, e.g., TSP-1 or TSP-2, or an agent which modulates TSP-21 or TSP-2, can be administered to a subject by standard methods. For example, the agent can be administered by any of a number of different routes including intravenous, intradermal, subcutaneous, oral (e.g., inhalation), transdermal (topical), and transmucosal. In one embodiment, the TSP-1 or TSP-2 or modulating agents thereof can be administered topically.

The agent which modulates TSP-1 or TSP-2 protein levels, e.g., TSP-1 or TSP-2 nucleic acid molecules, TSP-1 or TSP-2 polypeptides, fragments or analogs, TSP-1 or TSP-2 modulators, and anti-TSP-1 or TSP-2 antibodies (also referred to herein as "active compounds") can be incorporated into pharmaceutical compositions suitable for administration to a subject, e.g., a human. Such compositions typically include the nucleic acid molecule, polypeptide, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a TSP-1 or TSP-2 polypeptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. Such transdermal formulations can by applied to the skin to promote or inhibit hair growth.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., *PNAS* 91:3054–3057, 1994). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

The agent which modulates the level of angiogenesis, e.g., TSP-1 or TSP-2 polypeptide or fragment or analog thereof, can be administered by locally administration, e.g., topical administration. The agent can be applied once or it can be administered continuously, e.g., the agent is administered with sufficient frequency such that the effect on the TSP-1 or TSP-2 protein level is maintained for a selected period, e.g., 5, 10, 20, 30, 50, 90, 180, 365 days or more. The administration of an agent which modulates, e.g., increases or inhibits, the level of a TSP-1 or TSP-2 protein, e.g., a TSP-1 or TSP-2 polypeptide or fragment or analog thereof, can also be repeated.

Gene Therapy

Gene constructs of the invention can also be used as a part of a gene therapy protocol to deliver nucleic acids encoding either a positive or negative angiogenesis factor, e.g., an angiogenesis inhibitor, e.g., a TSP-1 or TSP-2 polypeptide or fragment or analog thereof. The invention features expression vectors for in vivo transfection and expression of a TSP-1 or TSP-2 polypeptide in particular cell types, e.g., epidermal cells, so as to inhibit angiogenesis, e.g., in the epidermis. Expression constructs of TSP-1 or TSP-2 polypeptides, may be administered in any biologically effective carrier, e.g. any formulation or composition capable of effectively delivering the TSP-1 or TSP-2 gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA, encoding a TSP-1 or TSP-2 polypeptide, or a VEGF antisense nucleic acid. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) *Blood* 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in *Current Protocols in Molecular Biology,* Ausubel, F. M. et al. (eds.) Greene Publishing Associates, (1989), Sections 9.10–9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) *Curr. Topics in Micro. and Immunol.* 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

In addition to viral transfer methods, such as those illustrated above, non-viral methods can also be employed to cause expression of a TSP-1 or TSP-2 polypeptide, fragment, or analog, in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject TSP-1 or TSP-2 gene by the targeted cell. Exemplary gene delivery systems of this type include liposomal derived systems, poly-lysine conjugates, and artificial viral envelopes. Other embodiments include plasmid injection systems such as are described in Meuli et al. (2001) *J Invest Dermatol.* 116(1):131–135; Cohen et al. (2000) *Gene Ther* 7(22):1896–905; or Tam et al. (2000) *Gene Ther* 7(21):1867–74.

In a representative embodiment, a gene encoding a TSP-1 or TSP-2 polypeptide, active fragment, or analog, can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075).

In clinical settings, the gene delivery systems for the therapeutic TSP-1 or TSP-2 gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Cell Therapy

TSP-1 or TSP-2 can also be increased in a subject by introducing into a cell, e.g., an epidermal cell, e.g., a keratinocyte, a nucleotide sequence that modulates the production of TSP-1 or TSP-2, e.g., a nucleotide sequence encoding a TSP-1 or TSP-2 polypeptide or functional fragment or analog thereof, a promoter sequence, e.g., a promoter sequence from a TSP-1 or TSP-2 gene or from another gene; an enhancer sequence, e.g., 5' untranslated region (UTR), e.g., a 5' UTR from a TSP-1 or TSP-2 gene or from another gene, a 3' UTR, e.g., a 3' UTR from a TSP-1 or TSP-2 gene or from another gene; a polyadenylation site; an insulator sequence; or another sequence that modulates the expression of TSP-1 or TSP-2. The cell can then be introduced into the subject.

Primary and secondary cells to be genetically engineered can be obtained form a variety of tissues and include cell types which can be maintained propagated in culture. For example, primary and secondary cells include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells (myoblasts) and precursors of these somatic cell types. Primary cells are preferably obtained from the individual to whom the genetically engineered primary or secondary cells are administered. However, primary cells may be obtained for a donor (other than the recipient) of the same species or another species (e.g., mouse, rat, rabbit, cat, dog, pig, cow, bird, sheep, goat, horse).

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. That is, the first time a plated primary cell is removed from the culture substrate and replated (passaged), it is referred to herein as a secondary cell, as are all cells in subsequent passages. Secondary cells are cell strains which consist of secondary cells which have been passaged one or more times. A cell strain consists of secondary cells that: 1) have been passaged one or more times; 2) exhibit a finite number of mean population doublings in culture; 3) exhibit the properties of contact-inhibited, anchorage dependent growth (anchorage-dependence does not apply to cells that are propagated in suspension culture); and 4) are not immortalized. A "clonal cell strain" is defined as a cell strain that is derived from a single founder cell. A "heterogenous cell strain" is defined as a cell strain that is derived from two or more founder cells.

Primary or secondary cells of vertebrate, particularly mammalian, origin can be transfected with an exogenous nucleic acid sequence which includes a nucleic acid sequence encoding a signal peptide, and/or a heterologous nucleic acid sequence, e.g., encoding TSP-1 or TSP-2, and produce the encoded product stably and reproducibly in vitro and in vivo, over extended periods of time. A heterologous amino acid can also be a regulatory sequence, e.g., a promoter, which causes expression, e.g., inducible expression or upregulation, of an endogenous TSP-1 or TSP-2 sequence. An exogenous nucleic acid sequence can be introduced into a primary or secondary cell by homologous recombination as described, for example, in U.S. Pat. No. 5,641,670, the contents of which are incorporated herein by reference.

The transfected primary or secondary cells may also include DNA encoding a selectable marker which confers a selectable phenotype upon them, facilitating their identification and isolation. Methods for producing transfected primary and secondary cells which stably express exogenous synthetic DNA, clonal cell strains and heterogeneous cell strains of such transfected cells, methods of producing the clonal heterogeneous cell strains, and methods of treating or preventing an abnormal or undesirable condition through the use of populations of transfected primary or secondary cells are part of the present invention.

Transfection of Primary or Secondary Cells of Clonal or Heterogeneous Cell Strains Vertebrate tissue can be obtained by standard methods such a punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. The exogenous nucleic acid sequence can optionally include DNA encoding a selectable marker. The exogenous nucleic acid sequence and selectable marker-encoding DNA can either be on separate constructs or on a single construct. An appropriate quantity of DNA is used to ensure that at least one stably transfected cell containing and appropriately expressing exogenous DNA is produced. In general, approximately 0.1 to 500 $\mu$g of DNA is used.

As used herein, the term "transfection" includes a variety of techniques for introducing an exogenous nucleic acid into a cell including calcium phosphate or calcium chloride precipitation, microinjection, DEAE-dextrin-mediated transfection, lipofection or electrophoration.

Electroporation is carried out at approximate voltage and capacitance (and corresponding time constant) to result in entry of the DNA construct(s) into the primary or secondary cells. Electroporation can be carried out over a wide range of voltages (e.g., 50 to 2000 volts) and corresponding capacitance. Total DNA of approximately 0.1 to 500 $\mu$g is generally used.

Methods such as calcium phosphate precipitation, modified calcium phosphate precipitation an polybrene precipitation, liposome fusion and receptor-mediated gene delivery can also be used to transect cells. Primary or secondary cells can also be transfected using microinjection. A stably, transfected cell can then be isolated and cultured and sub cultivated, under culturing conditions and for sufficient time to propagate stably transfected secondary cells an produce a clonal cell strain of transfected secondary cells. Alternatively, more than one transfected cell is cultured and sub cultured, resulting in production of a heterogeneous cell strain.

Transfected primary or secondary cells undergo sufficient number doubling to produce either a clonal cell strain or a heterogeneous cell strain of sufficient size to provide the therapeutic protein to an individual in effective amounts. In general, for example, 0.1 cm$^2$ of skin is biopsies and assumed to contain 1,000,000 cells; one cell is used to produce a clonal cell strain and undergoes approximately 27 doublings to produce 100 million transfected secondary cells. If a heterogeneous cell strain is to be produced from an original transfected population of approximately 1000,000 cells, only 10 doublings are needed to produce 100 million transfected cells.

The number of required cells in a transfected clonal heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient. The put these factors in perspective, to deliver therapeutic levels of human growth hormone in an otherwise healthy 10 kg patient with isolated growth hormone deficiency, approximately one to five hundred million transfected fibroblast would be necessary (the volume of these cells is about that of the very tip of the patient's thumb).

Implantation of Clonal Cell Strain or Heterogeneous Cell Strain of Transfected Secondary Cells The transfected cells, e.g., cells produced as described herein, can be introduced into an individual to whom the product is to be delivered. The clonal cell strain or heterogeneous cell strain is then introduced into an individual. Various routed of administration and various sites (e.g., renal sub capsular, subcutaneous, central nervous system (including intrathecal), intravascular, intrahepatic, intrasplanchnic, intraperitoneal (including intraomental), intramuscularly implantation) can be used. One implanted in individual, the transfected cells produce the product encoded by the heterologous DNA or are affected by the heterologous DNA itself. For example, an individual who suffers from hair loss is a candidate for implantation of TSP-1 or TSP-2 producing cells.

The individual can have a small skin biopsy performed; this is a simple procedure which can be performed on an outpatient basis. The piece of skin is taken, for example, from under the arm and can require about one minute to remove. The sample is processed, resulting in isolation of the patient's cell (e.g., fibroblasts) and genetically engineered to produce TSP-1 or TSP-2 or another protein or molecule that induces the production of TSP-1 or TSP-2. Based on the age, weight, and clinical condition of the patient, the required number of cells are grown in large-scale culture. The entire process should require 4–6 weeks and, at the end of that time, the appropriate number of genetically engineered cells are introduced into the individual, once again as an outpatient (e.g., by injecting them back under the patient's skin, e.g., on the scalp or face). The patient is now capable of producing TSP-1 or TSP-2 which can prevent or reduce wrinkles.

For some, this will be a one-time treatment and, for others, multiple cell therapy treatments will be required.

As this example suggests, the cells used will generally be patient-specific genetically engineered cells. It is possible, however, to obtain cells from another individual of the same species or from a different species. Use of such cells might require administration of an immunosuppressant, alteration of histocompatibility antigens, or use of a barrier device to prevent rejection of the implanted cells.

Transfected primary or secondary cells can be administered alone or in conjunction with a barrier or agent for inhibiting immune response against the cell in a recipient subject. For example, an immunosuppressive agent can be administered to a subject to inhibit or interfere with normal response in the subject. Preferably, the immunosuppressive agent is an immunosuppressive drug which inhibits T cell/or B cell activity in a subject. Examples of such immunosuppressive drugs commercially available (e.g., cyclosporin A is commercially avail for Sandoz Corp. East Hanover, N.J.).

An immunosuppressive agent e.g., drug, can be administered to a subject at a dosage sufficient to achieve the desired therapeutic effect (e.g., inhibition of rejection of the cells). Dosage ranges for immunosuppressive drugs are known in the art. See, e.g., Freed et al. (1992) *N. Engl. J. Med.* 327:1549; Spencer et al. (1992) *N. Engl. J. Med.* 327:1541' Widner et al. (1992) *n. Engl. J. Med.* 327:1556). Dosage values may vary according to factors such as the disease state, age, sex, and weight of the individual.

Another agent with can be used to inhibit T cell activity in a subject is an antibody, or fragment of derivative thereof. Antibodies capable of depleting or sequestering T cells in vivo are known in the art. Polyclonal antisera can be used, for example, anti-lymphocyte serum. Alternatively, one or more monoclonal antibodies can be used. Preferred T cell depleting antibodies include monoclonal antibodies which bind to CD2, CD3, CD4, CD8, CD40, CD40, ligand on the cell surface. Such antibodies are known in the art and are commercially available, for example, form American Type Culture Collection. A preferred antibody for binding CD3 on human T cells is OKT3 (ATCC CRL 8001).

An antibody which depletes, sequesters or inhibits T cells within a recipient subject can be administered in a dose for an appropriate time to inhibit rejection of cells upon transplantation. Antibodies are preferably administered intravenously in a pharmaceutically acceptable carrier of diluent (e.g., saline solution).

Another way of interfering with or inhibiting an immune response to the cells in a recipient subject is to use an immunobarrier. An "immunobarrier" as used herein, refers to a device which serves as a barrier between the administered cell and cells involved in immune response in a subject. For example, the cells can be administered in an implantable device. An implantable device can include the cells contained within a semi-permeable barrier, i.e., one which lets nutrients and the product diffuse in and out of the barrier but which prevents entry or larger immune system components, e.g., antibodies or complement. An implantable device typically includes a matrix, e.g., a hydrogel, biocompatible mesh, or core in which cells are disposed. Optionally, a semi permeable coating can enclose the gel. If disposed within the gel core, the administered cells should be sequestered from the cells of the immune system and should be cloaked from the cells and cytotoxic antibodies of the host. Preferably, a permselective coating such as PLL or PLO is used. The coating often has a porosity which prevents components of the recipient's immune system from entering and destroying the cells within the implantable device.

Many methods for encapsulating cells are known in the art. For example, encapsulation using a water soluble gum to obtain a semi-permeable water insoluble gel to encapsulate cells for production and other methods of encapsulation are disclosed in U.S. Pat. No. 4,352,883. Other implantable devices which can be used are disclosed in U.S. Pat. Nos. 5,084,350, 5,427,935, WO 95/19743 published Jul. 27, 1995, U.S. Pat. Nos. 5,545,423, 4,409,331, 4,663,286, and European Patent No. 301,777.

An advantage of the use of transfected or secondary cells is that by controlling the number of cells introduced into an individual, one can control the amount of the protein delivered to the body. In addition, in some cases, it is possible to remove the transfected cells of there is no longer a need for the product. A further advantage of treatment by use of transfected primary or secondary cells of the present invention is that production of the therapeutic product can be regulated, such as through the an administration of zinc, steroids or an agent which affects transcription of a protein, product or nucleic acid product or affects the stability of a nucleic acid product.

EXAMPLES

Example 1

Enhanced Skin Angiogenesis After Long-Term UVB Irradiation

After ten weeks of UVB irradiation (cumulative dose: 5.65 $J/cm^2$), replicas were obtained from the back skin of UVB irradiated and of non-irradiated mice in order to evaluate the skin surface relief as a parameter for the extent of skin damage. Pronounced formation of wrinkles was observed in UVB irradiated mice, whereas no visible wrinkles were detected in non-irradiated control mice. Macroscopic examination of the underside of the skin demonstrated increased subcutaneous vascularization in UVB-irradiated mice with enlarged blood vessels and increased vessel branching.

Histological analysis showed thickening of the epidermis, dermis and sebaceous glands (36) in UVB-treated mice, accompanied by accumulation of inflammatory cells in the upper dermis. Moreover, we found fragmented and less organized collagen fibers and elastic fibers in UVB irradiated skin, as compared with the regular pattern observed in non-irradiated control skin. Immunostains for CD31 revealed an increased number of enlarged blood vessels in the dermis of UVB irradiated mice, as compared with untreated controls. These changes were most prominent in the papillary dermis, in an area immediately underlying the epidermis. Differential immunofluorescent stainings for the proliferation marker Ki67 and for the endothelial junction molecule CD31 revealed a greatly increased number of proliferative endothelial cells in the enlarged blood vessels in UVB irradiated skin, whereas proliferating endothelial cells were rarely detected in control skin. The highest rate of endothelial cell proliferation was observed in the upper dermis of UVB irradiated skin. In non-irradiated epidermis, proliferating epidermal keratinocytes were selectively detected in the basal layer. In contrast, a large number of proliferating keratinocytes was found in the suprabasal layers of the hyperplastic epidermis after UVB irradiation.

A quantitative, computer-assisted morphometric analysis of cutaneous vessel density and size was performed, using CD31-stained tissue sections. Chronic UVB irradiation resulted in a significant ($p<0.001$) increase in vascular density, as compared with non-irradiated controls. Vessels in UVB irradiated skin were also significantly larger ($p<0.001$) with a 67% increase in size, leading to a more than 130% increase ($p<0.001$) in the cutaneous area covered by vessels.

Example 2

Enhanced Epidermal VEGF Expression After Long-Term UVB Irradiation

The effect of long-term UVB irradiation on cutaneous VEGF mRNA expression was examined. Using in situ hybridization, it was found that VEGF mRNA expression was potently upregulated in suprabasal epidermal keratinocytes after long-term UVB irradiation, whereas little or no VEGF mRNA expression was detected in the skin of non-UVB irradiated mice.

Example 3

Overexpression of TSP-1 Prevents UVB-Induced Cutaneous Damage, Wrinkle Formation and Angiogenesis To characterize the biological significance of cutaneous angiogenesis for the effects of long-term UVB irradiation, transgenic mice with skin-specific overexpression of the endogenous angiogenesis inhibitor TSP-1 were subjected to the same UVB irradiation regimen. These mice have been previously characterized in detail and show potent inhibition of induced angiogenesis (24). After 10 weeks of UVB irradiation (cumulative UVB dose of 6.52 $J/cm^2$), all wild-type mice showed pronounced wrinkle formation on the their dorsal skin. In contrast, little or no wrinkle formation was observed in TSP-1 overexpressing transgenic mice. Macroscopically, K14/TSP-1 transgenic mice also showed reduced skin vascularization, as compared with wildtype littermates.

Histological analysis revealed that the UVB-induced thickening of the dermis and the subcutis, but not of the epidermis, was less pronounced in K14/TSP-1 transgenic mice, as compared with wildtype mice. A concomitant reduction of inflammatory cell infiltration was also found and a more regular arrangement and structure of collagen fibers was found in the dermis of K14/TSP-1 transgenic mice as compared to wildtype mice. Moreover, the skin vascular was greatly reduced in K14/TSP-1 transgenic mice. Morphometric analysis of CD31 stained skin sections showed a more than 55% reduction of vessel sizes in TSP-1 transgenic mice ($p<0.001$) and a significant reduction in the cutaneous area covered by vessels ($p<0.001$). No significant reduction of the vessel density was detected in TSP-1 transgenic mice. Double immunofluorescent stainings for CD31 and Ki-67 demonstrated a marked reduction in the number of proliferating endothelial cells in the dermis of UVB irradiated TSP-1 transgenic mice, as compared with UVB irradiated wildtype littermates. Moreover, TUNEL assays, combined with CD31 stainings, revealed an increased number of apoptotic endothelial cells in the skin of TSP-1 transgenic mice, as compared with wildtype littermates.

Example 4

Overexpression of TSP-1 Prevents UVB-Induced MMP-9 Activation

Matrix metalloproteinase-9 (MMP-9) has been implicated in mediating UVB-induced degradation of extracellular matrix components (35), and it has been recently suggested that MMP-9 activity plays a crucial role in angiogenesis by controlling the bioavailability of VEGF (37). Wildtype and TSP-1 transgenic mice were subjected to a single-dose UVB irradiation (126 mJ/cm$^2$) of the back skin and MMP-9 activity was determined in skin lysates by gelatin zymography. Single-dose UVB irradiation of wildtype mice resulted in markedly enhanced subcutaneous vascularization after 24 h which was less pronounced in TSP-1 transgenic mice. Gelatin zymography demonstrated equal levels of MMP-9 activity in the normal skin of wildtype and TSP-1 transgenic mice. 24 h after UVB irradiation, however, MMP-9 activity was strongly increased in the skin of wildtype mice but was diminished in TSP-1 transgenic mice.

Example 5

TSP-2 Knock Out Mice Show Increased Wrinkle Formation

Long-term UVB irradiation (cumulative UVB dose: 7.23 J/cm$^2$) produces pronounced wrinkle formation in TSP-2 deficient mice, as compared with wildtype mice. Enlarged cutaneous blood vessels and enhanced vascular branching was seen in TSP-2 deficient mice after chronic UVB irradiation, as compared with wildtype littermates.

Hematoxylin-eosin stains revealed thickening of epidermis and dermis in the skin of TSP-2 deficient mice after long-term UVB irradiation, as compared with wildtype control skin. Trichrome stains demonstrated irregular organization of collagen fibers in the papillary dermis of TSP-2 deficient after chronic UVB irradiation, as compared with wildtype mice. CAE stains revealed increased inflammatory cell infiltration in TSP-2 deficient mice, as compared with wildtype mice.

Immunostains for CD31 revealed more numerous and enlarged blood vessels in the total (dermis+subcutis) skin and in the upper dermis of TSP-2 deficient mice after chronic UVB irradiation, as compared with wildtype littermates. Computer-assisted image analysis of CD31 stained sections revealed a significant increase in vessel size and vessel density in the total skin of TSP-2 deficient mice after chronic UVB irradiation, as compared with wildtype littermates. Similar to vascularization in total skin, the vascularization was also significantly increased in the upper dermis, within a distance of 100 μm from the epidermal-dermal border in TSP-2 deficient mice after chronic UVB irradiation.

Double immunoflorescent stains for CD31 and BrdU revealed a pronounced increase in the number of proliferative endothelial cells (arrows) in the upper dermis and the lower dermis of the skin of TSP-2 deficient mice, as compared with wildtype mice.

In situ hybridization for VEGF demonstrated enhanced VEGF mRNA expression in suprabasal keratinocytes of the hyperplastic epidermis in TSP-2 deficient mice after chronic UVB irradiation, as compared with little or no VEGF mRNA expression in wildtype epidermis.

Gelatin-zymography reveals strong induction of MMP-9 activity in the skin of UVB irradiated wildtype mice as compared with non-irradiated wildtype mice. No major differences in MMP-9 activity were detected between TSP-2 deficient mice and wildtype mice after chronic UVB irradiation.

Example 6

Methods and Materials

UVB Irradiation Regimen.

In a first experiment, 8-week-old female hairless Skh-1 mice (n=7 per group) were exposed to UVB irradiation, using a bank of 4 equally spaced fluorescent lamps (Elder Pharmaceuticals, Bryan, Ohio) (25). The height of the lamps was adjusted to deliver 0.35 mW/cm2 at the dorsal skin surface of the mice. Mice were irradiated with UVB trice weekly for ten weeks, with a starting dose of 0.5 minimal erythema dose (20 mJ/cm2) and gradual increases in increments of 0.5 MED to a maximum dose of 4.5 MED (26). The total cumulative dose of UVB was 5.62 J/cm2. No acute sun burn reactions were observed. Control mice were sham-irradiated. In an additional experiment, 8-week-old female K14/TSP-1 transgenic mice (24) or FVB wildtype controls (n=7 per group) were treated with UVB irradiation as described above for a total of 12 weeks (cumulative UVB dose 6.52 J/cm2). After 12 weeks, mice were sacrificed and skin replicas were obtained using silicon rubber (SILFLO; Flexico Developments Ltd, U.K.) as described (27). Back skin samples were either snap-frozen in liquid nitrogen or fixed in 10% formaldehyde as described (28). All animal studies were approved by the Massachusetts General Hospital Subcommittee on Research Animal Care.

Immunohistochemistry for CD31 and Computer-Assisted Morphometric Analysis of Cutaneous Blood Vessels.

Immunohistochemical stainings were performed on 7 μm frozen sections as described (24), using a monoclonal rat anti-mouse CD31 antibody (Pharmingen, San Diego, Calif.). Representative sections were obtained from five UVB irradiated mice and from five age-matched, non-UVB irradiated control mice, and were analyzed using a Nikon E-600 microscope (Nikon; Melville, N.Y.). Images were captured with a Spot digital camera (Diagnostic Instruments, Sterling Heights, Mich.), and morphometric analyses were performed using the IP-LAB software (Scanalytics Inc, Fairfax, Va.) as described (24). Three different fields of each section were examined at 60× magnification, and the number of vessels per mm$^2$, the average vessel size and the relative area occupied by blood vessels were determined in the dermis, in an area within 100 μm distance from the epidermal-dermal junction. The two-sided unpaired Student's t-test was used to analyze differences in microvessel density and vascular size. In addition, paraffin sections were obtained from the skin of the same mice and routine hematoxylin-eosin, Verhoeff's elastic and Weigert's resorcin fuchsin stains were performed as described (29)

Proliferation and Apoptosis Assays.

To analyze endothelial cell proliferation, double immunofluorescent stainings for the endothelial cell marker CD31 and the proliferation marker Ki-67 (30, 31) were performed on 7 μm frozen sections, using a monoclonal rat anti-mouse CD31 antibody and a rabbit anti-Ki-67 polyclonal antibody (Novocastra Laboratories, Burlingame, Calif.). Anti-rat IgG conjugated with FITC and anti-rabbit IgG conjugated with Texas-Red (Jackson ImmunoResearch Laboratories, West Grove, Pa.) were used as secondary antibodies (32). Representative sections were obtained from five mice for each experimental group and were analyzed using a Nikon E-600 microscope. Digital images of CD31 and Ki-67 stains were obtained in identical fields and were combined to reveal proliferative endothelial cells. Apoptotic endothelial cells were detected by double immunofluorescence, using the Fluorescence-FragEL DNA fragmentation detection kit (Oncogene, Cambridge, Mass.) and an anti-mouse CD31 antibody together with an anti-rat IgG conjugated with Texas-Red as described (24).

In Situ Hybridization.

In situ hybridization was performed on paraffin sections as described (19). Briefly, slides were processed through xylene to remove paraffin, then passed sequentially though graded alcohols; 0.2M HCl; Tris/EDTA with 3 µg/ml proteinase K; 0.2% glycine; 4% paraformaldehyde in phosphate-buffered saline pH 7.4; 0.1M triethanolamine containing 1/200 (vol/vol) acetic anhydride; and 2× SSC. Slides were hybridized overnight at 52•C with 35S labeled riboprobes in the following mixture: 0.3M NaCl, 0.01M Tris pH 7.6, 5 mM EDTA, 50% formamide, 10% dextran sulfate, 0.1 mg/ml yeast tRNA, and 0.01M dithiothreitol. Post-hybridization washes included 2× SSC/50% formamide/10 mM dithiothreitol at 65•C and 2× SSC. Slides were then dehydrated though graded alcohol containing 0.3M ammonium acetate, dried, coated with Kodak NTB2 emulsion and stored in the dark at 4•C for 2 weeks. The emulsion was developed with Kodak 19 developer and the slides were counterstained with hematoxylin. Antisense and sense single-stranded 35S-labeled RNA probes for VEGF were prepared from a 393-bp rat VEGF cDNA fragment (12), cloned into pGEM-3Z (Promega).

Gelatin Zymography.

The shaved back skin of wildtype FVB mice and transgenic mice (n=4 per group) was exposed to a single dose of UVB irradiation (126 mJ/cm2). After 24 h, mice were sacrificed and back skin samples were excised and homogenized in extraction buffer (0.05M Tris/pH 7.5, 0.2M NaCl, 5 mM CaCl2, 0.1% Triton X-100). After centrifugation, supernatants were collected for gelatin-zymography. Zymography was performed as described (33, 34) with minor modifications. Briefly, skin lysates were resuspended in non-reducing 4× SDS sample buffer (0.5M Tris-HCl/pH 6.8, 0.02% bromophenol blue, 40% (v/v) glycerol, 3% SDS) and were loaded onto SDS polyacrylamide gels containing 0.1% pork skin gelatin (SIGMA). Twenty µg of each protein lysate were subjected to SDS-PAGE. The gels were incubated with 2.5% Triton X-100 to remove SDS and then overnight with incubation buffer (0.05M Tris-HCl/pH 8.0, 5 mM CaCl2, 5 µM ZnCl). Gels were then stained with a 0.5% Coomassie brilliant blue R-250/30% methanol/10% acetic acid solution, followed by destaining using a 30% methanol/10% acetic acid solution. MMP-9 activity was detected as a band of 92 kDa molecular weight (35).

1. Kripke, M. L. 1994. Ultraviolet radiation and immunology: something new under the sun—presidential address. *Cancer Res.* 54:6102–6105.

2. Cox, N. H., B. L. Diffey, and P. M. Farr. 1992. The relationship between chronological age and the erythemal response to ultraviolet B radiation. *Br J Dermatol.* 126:315–319.

3. Pearse, A. D., S. A. Gaskell, and R. Marks. 1987. Epidermal changes in human skin following irradiation with either UVB or UVA. *J Invest Dermatol.* 88:83–87.

4. Berton, T. R., D. L. Mitchell, S. M. Fischer, and M. F. Locniskar. 1997. Epidermal proliferation but not quantity of DNA photodamage is correlated with UV-induced mouse skin carcinogenesis. *J Invest Dermatol.* 109:340–347.

5. Leyden, J. J., G. L. Grove, M. J. Grove, E. G. Thorne, and L. Lufrano. 1989. Treatment of photodamaged facial skin with topical tretinoin. *J Am Acad Dermatol.* 21:638–644.

6. Kligman, A. M. 1989. The treatment of photoaged human skin by topical tretinoin. *Drugs.* 38:1–8.

7. Bielenberg, D. R., C. D. Bucana, R. Sanchez, C. K. Donawho, M. L. Kripke, and I. J. Fidler. 1998. Molecular regulation of UVB-induced cutaneous angiogenesis. *J Invest Dermatol.* 111:864–872.

8. Kramer, M., C. Sachsenmaier, P. Herrlich, and H. J. Rahmsdorf. 1993. UV irradiation-induced interleukin-1 and basic fibroblast growth factor synthesis and release mediate part of the UV response. *J Biol Chem.* 268:6734–6741.

9. Strickland, I., L. E. Rhodes, B. F. Flanagan, and P. S. Friedmann. 1997. TNF-alpha and IL-8 are upregulated in the epidermis of normal human skin after UVB exposure: correlation with neutrophil accumulation and E-selectin expression. *J Invest Dermatol.* 108:763–768.

10. Yano, K., L. F. Brown, and M. Detmar. 2001. Control of hair growth and follicle size by VEGF-mediated angiogenesis. *J Clin Invest.* 107:409–417.

11. Detmar, M. 1996. Molecular regulation of angiogenesis in the skin. *J. Invest. Dermatol.* 106:207–208.

12. Detmar, M., L. F. Brown, K. P. Claffey, K. -T. Yeo, O. Kocher, R. W. Jackman, B. Berse, and H. F. Dvorak. 1994. Overexpression of vascular permeability factor/vascular endothelial growth factor and its receptors in psoriasis. *J. Exp. Med.* 180:1141–1146.

13. Brown, L. F., K. T. Yeo, B. Berse, T. K. Yeo, D. R. Senger, H. F. Dvorak, and L. Van De Water. 1992. Expression of vascular permeability factor (vascular endothelial growth factor) by epidermal keratinocytes during wound healing. *J. Exp. Med.* 176:1375–1379.

14. Brown, L. F., T. J. Harrist, K. -T. Yeo, M. Stahle-Backdahl, R. W. Jackman, B. Berse, K. Tognazzi, H. F. Dvorak, and M. Detmar. 1995. Increased expression of vascular permeability factor (vascular endothelial growth factor) in bullous pemphigoid, dermatitis herpetiformis, and erythema multiforme. *J Invest Dermatol.* 104:744–749.

15. Brown, L. F., S. M. Olbricht, B. Berse, R. W. Jackman, G. Matsueda, K. A. Tognazzi, E. J. Manseau, H. F. Dvorak, Van, de, Water, and L. 1995. Overexpression of vascular permeability factor (VPF/VEGF) and its endothelial cell receptors in delayed hypersensitivity skin reactions. *J Immunol.* 154:2801–2807.

16. Detmar, M., L. F. Brown, M. P. Schön, B. M. Elicker, P. Velasco, L. Richard, D. Fukumura, W. Monsky, K. P. Claffey, and R. K. Jain. 1998. Increased microvascular density and enhanced leukocyte rolling and adhesion in the skin of VEGF transgenic mice. *J. Invest. Dermatol.* 111:1–6.

17. Detmar, M. 2000. The role of VEGF and thrombospondins in skin angiogenesis. *J Dermatol Sci.* 24 Suppl 1:S78–S84.

18. Tolsma, S. S., O. V. Volpert, D. J. Good, W. A. Frazier, P. J. Polverini, and N. Bouck. 1993. Peptides derived from two separate domains of the matrix protein thrombospondin-1 have anti-angiogenic activity. *J. Cell Biol.* 122:497–511.

19. Streit, M., P. Velasco, L. F. Brown, M. Skobe, L. Richard, L. Riccardi, J. Lawler, and M. Detmar. 1999. Overexpression of thrombospondin-1 decreases angiogenesis and inhibits the growth of human cutaneous squamous cell carcinomas. *Am J Pathol.* 155:441–452.

20. Wight, T. N., G. J. Raugi, S. M. Mumby, and P. Bornstein. 1985. Light microscopic immunolocation of thrombospondin in human tissues. *J. Histochem. Cytochem.* 33:295–302.

21. Bissett, D. L., D. P. Hannon, and T. V. Orr. 1987. An animal model of solar-aged skin: histological, physical, and visible changes in UV-irradiated hairless mouse skin. *Photochem Photobiol.* 46:367–378.

22. Kligman, L. H., C. H. Duo, and A. M. Kligman. 1984. Topical retinoic acid enhances the repair of ultraviolet damaged dermal connective tissue. *Connect Tissue Res.* 12:139–150.

23. Lavker, R. M., and A. M. Kligman. 1988. Chronic heliodermatitis: a morphologic evaluation of chronic actinic dermal damage with emphasis on the role of mast cells. *J Invest Dermatol.* 90:325–330.

24. Streit, M., P. Velasco, L. Riccardi, L. Spencer, L. F. Brown, L. Janes, B. Lange-Asschenfeldt, K. Yano, T. Hawighorst, L. Iruela-Arispe, and M. Detmar. 2000. Thrombospondin-1 suppresses wound healing and granulation tissue formation in the skin of transgenic mice. *EMBO J.* 19:3272–3282.

25. Kochevar, I. E., M. Moran, N. Lyon, T. Flotte, E. Siebert, and R. W. Gange. 1993. Effects of systemic indomethacin, meclizine, and BW755C on chronic ultraviolet B-induced effects in hairless mouse skin. *J Invest Dermatol.* 100:186–193.

26. Kligman, L. H. 1989. The ultraviolet-irradiated hairless mouse: a model for photoaging. *J Am Acad Dermatol.* 21:623–631.

27. Chen, S., I. Kiss, and K. M. Tramposch. 1992. Effects of all-trans retinoic acid on UVB-irradiated and non-irradiated hairless mouse skin. *J Invest Dermatol.* 98:248–254.

28. Streit, M., L. Riccardi, P. Velasco, L. F. Brown, T. Hawighorst, P. Bornstein, and M. Detmar. 1999. Thrombospondin-2: a potent endogenous inhibitor of tumor growth and angiogenesis. *Proc Natl Acad Sci U S A.* 96:14888–14893.

29. Prophet, E., B. Mills, J. Arrington, and L. Sobin. 1992. Laboratory Methods in Histotechnology. American Registry of Pathology, Washington, D. C. 236–237 pp.

30. Key, G., M. H. Becker, B. Baron, M. Duchrow, C. Schluter, H. D. Flad, and J. Gerdes. 1993. New Ki-67-equivalent murine monoclonal antibodies (MIB 1–3) generated against bacterially expressed parts of the Ki-67 cDNA containing three 62 base pair repetitive elements encoding for the Ki-67 epitope. *Lab Invest.* 68:629–636.

31. Gerdes, J., U. Schwab, H. Lemke, and H. Stein. 1983. Production of a mouse monoclonal antibody reactive with a human nuclear antigen associated with cell proliferation. *Int J Cancer.* 31:13–20.

32. Skobe, M., P. Rockwell, N. Goldstein, S. Vosseler, and N. E. Fusenig. 1997. Halting angiogenesis suppresses carcinoma cell invasion. *Nat Med.* 3:1222–1227.

33. Delclaux, C., C. Delacourt, M. P. D'Ortho, V. Boyer, C. Lafuma, and A. Harf. 1996. Role of gelatinase B and elastase in human polymorphonuclear neutrophil migration across basement membrane. *Am J Respir Cell Mol Biol.* 14:288–295.

34. Hanemaaijer, R., P. Koolwijk, L. le Clercq, W. J. de Vree, and V. W. van Hinsbergh. 1993. Regulation of matrix metalloproteinase expression in human vein and microvascular endothelial cells. Effects of tumour necrosis factor alpha, interleukin 1 and phorbol ester. *Biochem J.* 296:803–809.

35. Koivukangas, V., M. Kallioinen, H. Autio-Harmainen, and A. Oikarinen. 1994. UV irradiation induces the expression of gelatinases in human skin in vivo. *Acta Derm Venereol.* 74:279–282.

36. Lesnik, R. H., L. H. Kligman, and A. M. Kligman. 1992. Agents that cause enlargement of sebaceous glands in hairless mice. II. Ultraviolet radiation. *Arch Dermatol Res.* 284:106–108.

37. Bergers, G., R. Brekken, G. McMahon, T. H. Vu, T. Itoh, K. Tamaki, K. Tanzawa, P. Thorpe, S. Itohara, Z. Werb, and D. Hanahan. 2000. Matrix metalloproteinase-9 triggers the angiogenic switch during carcinogenesis. *Nat Cell Biol.* 2:737–744.

38. Kligman, A. M., G. L. Grove, R. Hirose, and J. J. Leyden. 1986. Topical tretinoin for photoaged skin. *J Am Acad Dermatol.* 15:836–859.

39. Dejana, E., M. Corada, and M. G. Lampugnani. 1995. Endothelial cell-to-cell junctions. *FASEB J.* 9:910–918.

40. Detmar, M., K. -T. Yeo, J. A. Nagy, L. Van De Water, L. F. Brown, B. Berse, B. M. Elicker, S. Ledbetter, and H. F. Dvorak. 1995. Keratinocyte-derived vascular permeability factor (vascular endothelial growth factor) is a potent mitogen for dermal microvascular endothelial cells. *J. Invest. Dermatol.* 105:44–50.

41. Brown, L. F., S. M. Olbricht, B. Berse, R. W. Jackman, G. Matsueda, K. A. Tognazzi, E. J. Manseau, H. F. Dvorak, and L. Van de Water. 1995. Overexpression of vascular permeability factor (VPF/VEGF) and its endothelial cell receptors in delayed hypersensitivity skin reactions. *J Immunol.* 154:2801–2807.

42. Kishimoto, J., R. Ehama, Y. Ge, T. Kobayashi, T. Nishiyama, M. Detmar, and R. E. Burgeson. 2000. In vivo detection of human vascular endothelial growth factor promoter activity in transgenic mouse skin. *Am J Pathol.* 157:103–110.

43. Brauchle, M., J. O. Funk, P. Kind, and S. Werner. 1996. Ultraviolet B and H2O2 are potent inducers of vascular endothelial growth factor expression in cultured keratinocytes. *J Biol Chem.* 271:21793–21797.

44. White, F. C., A. Benehacene, J. S. Scheele, and M. Kamps. 1997. VEGF mRNA is stabilized by ras and tyrosine kinase oncogenes, as well as by UV radiation—evidence for divergent stabilization pathways. *Growth Factors.* 14:199–212.

45. Yuan, F., Y. Chen, M. Dellian, N. Safabakhsh, N. Ferrara, and R. K. Jain. 1996. Time-dependent vascular regression and permeability changes in established human tumor xenografts induced by an anti-vascular endothelial growth factor/vascular permeability factor antibody. *Proc Natl Acad Sci U S A.* 93:14765–14770.

46. Jimenez, B., O. V. Volpert, S. E. Crawford, M. Febbraio, R. L. Silverstein, and N. Bouck. 2000. Signals leading to apoptosis-dependent inhibition of neovascularization by thrombospondin-1. *Nat Med.* 6:41–48.

47. Yang, Z., D. K. Strickland, and P. Bornstein. 2000. Extracellular MMP2 levels are regulated by the LRP scavenger receptor and thrombospondin 2. *J Biol Chem.* 11:11.

48. Bein, K., and M. Simons. 2000. Thrombospondin type 1 repeats interact with matrix metalloproteinase 2. Regulation of metalloproteinase activity. *J Biol Chem.* 275:32167–32173.

49. Taraboletti, G., L. Sonzogni, V. Vergani, G. Hosseini, R. Ceruti, C. Ghilardi, A. Bastone, E. Toschi, P. Borsotti, E. Scanziani, R. Giavazzi, M. S. Pepper, W. G. Stetler-Stevenson, and M. R. Bani. 2000. Posttranscriptional stimulation of endothelial cell matrix metalloproteinases 2 and 1 by endothelioma cells. *Exp Cell Res.* 258:384–394.

50. Kang, S. 1998. Photoaging and tretinoin. *Dermatol Clin.* 16:357–364.

51. Fisher, G. J., Z. Q. Wang, S. C. Datta, J. Varani, S. Kang, and J. J. Voorhees. 1997. Pathophysiology of premature skin aging induced by ultraviolet light. *N Engl J Med.* 337:1419–1428.

Other Embodiments

It is understood that while the invention has been described in conjunction with the detailed description thereof, the foregoing description and examples are intended to illustrate and not limit the scope of the invention, which is defined by the scope of the appended claims. Other aspects, advantages, and modifications are within the scope of the claims.

All patents and references cited herein are incorporated in their entirety by reference. Other embodiments are within the following claims.

We claim:

1. A method of reducing long-term UVB-induced wrinkles in a subject, comprising:

identifying a subject in need of wrinkle prevention; and inhibiting angiogenesis in the skin of the subject, thereby reducing long-term UVB-induced wrinkles in a subject.

2. The method of claim 1, wherein angiogenesis is inhibited by increasing TSP-2 or TSP-1 activity in the subject.

3. The method of claim 1, wherein angiogenesis is inhibited by administering to the subject a compound that induces an anti-angiogenesis factor.

4. The method of claim 3, wherein the anti-angiogenesis factor is TSP-1 or TSP-2.

5. The method of claim 1, wherein the method comprises administering to the subject a composition comprising an inhibitor of angiogenesis or an agent which induces an inhibitor of angiogenesis in an amount sufficient to reduce or prevent said wrinkle.

6. The method of claim 5, wherein the wrinkle is caused by exposure to natural sunlight.

7. The method of claim 5, wherein the inhibitor of angiogenesis is administered topically.

8. The method of claim 5, wherein the inhibitor of angiogenesis is provided in a sterile composition.

9. The method of claim 5, wherein the inhibitor of angiogenesis is TSP-2 or TSP-1.

10. A method of providing protection against long-term UVB induced wrinkles to a subject, said method comprising:

supplying to the subject a composition comprising an inhibitor of angiogenesis or an agent that induces an inhibitor of angiogenesis; and supplying to the subject instructions for using said composition to prevent wrinkles.

11. The method of claim 10, wherein the inhibitor of angiogenesis is TSP-2 or TSP-1.

12. The method of claim 10, wherein said instructions comprise directions to apply the composition to the skin prior to sun exposure.

13. The method of claim 10, wherein the composition further comprises a cosmetic ingredient.

14. A kit for reducing long-term UVB induced wrinkles in a subject, said kit comprising:

a composition comprising an inhibitor of angiogenesis or an agent that induces an inhibitor of angiogenesis; and instructions for using the composition to reduce wrinkles.

15. The kit of claim 14, wherein said inhibitor of angiogenesis is TSP-1 or TSP-2.

16. The kit of claim 14, wherein said composition further comprises a cosmetic ingredient.

17. The kit of claim 14, wherein said instructions comprise directions to apply said composition to the skin prior to or during sun exposure.

* * * * *

UNITED STATES PATENT AND TRADEMARK OFFICE
CERTIFICATE OF CORRECTION

| | | |
|---|---|---|
| PATENT NO. | : 6,712,617 B2 | Page 1 of 2 |
| APPLICATION NO. | : 10/122263 | |
| DATED | : March 30, 2004 | |
| INVENTOR(S) | : Michael J. Detmar and Kiichiro Yano | |

It is certified that error appears in the above-identified patent and that said Letters Patent is hereby corrected as shown below:

Column 1, line 3, insert the following paragraph -- This invention was made with Government support under Grant Number CA86410 awarded by the National Institutes of Health. The Government has certain rights in this invention.--;

Column 8, line 55, replace "or a more" with --or more--;

Column 17, line 37, replace "may" with --many--;

Column 27, line 34, replace "form" with --from--;

Column 28, line 32, replace "a" with --as--;

Column 28, line 67, replace "an" with --and--;

Column 29, line 7, replace "an" with --and--;

Column 29, line 20, replace "1000, 000" with --1,000,000--;

Column 29, line 31, replace "The put" with --To put--;

Column 29, line 47, replace "One" with --Once--;

Column 30, line 31, replace "with" with --that--;

Column 31, line 17, replace "cells of" with --cells if--;

Column 31, line 21, delete "an";

Column 32, line 32, delete "the";

UNITED STATES PATENT AND TRADEMARK OFFICE
CERTIFICATE OF CORRECTION

PATENT NO. : 6,712,617 B2
APPLICATION NO. : 10/122263
DATED : March 30, 2004
INVENTOR(S) : Michael J. Detmar and Kiichiro Yano It is certified that error appears in the above-identified patent and that said Letters Patent is hereby corrected as shown below:

Column 40, line 27, insert the following claims:

--18. The method of claim 1, wherein angiogenesis is inhibited by administering TSP-1 to the subject.
 19. The method of claim 1, wherein angiogenesis is inhibited by administering TSP-2 to the subject.
 20. The method of claim 5, wherein the composition comprises TSP-1.
 21. The method of claim 5, wherein the composition comprises TSP-2.
 22. The method of claim 10, wherein the composition comprises TSP-1.
 23. The method of claim 10, wherein the composition comprises TSP-2.--.

Signed and Sealed this

Tenth Day of July, 2007

JON W. DUDAS
*Director of the United States Patent and Trademark Office*